(12) United States Patent
Thalgott et al.

(10) Patent No.: US 7,156,805 B2
(45) Date of Patent: Jan. 2, 2007

(54) SURGICAL RETRACTOR

(75) Inventors: John Thalgott, Las Vegas, NV (US); Michael J. Mahoney, Middletown, RI (US)

(73) Assignee: DePuy Spine, Inc., Raynham, MA (US)

( * ) Notice: Subject to any disclaimer, the term of this patent is extended or adjusted under 35 U.S.C. 154(b) by 121 days.

(21) Appl. No.: 10/405,063

(22) Filed: Mar. 31, 2003

(65) Prior Publication Data

US 2004/0193018 A1  Sep. 30, 2004

(51) Int. Cl.
*A61B 1/32* (2006.01)
*A61B 1/00* (2006.01)

(52) U.S. Cl. ............... 600/227; 600/234; 600/228; 600/102

(58) Field of Classification Search ........... 600/227, 600/210, 228, 229, 230, 231, 323, 233, 215, 600/201, 234, 102
See application file for complete search history.

(56) References Cited

U.S. PATENT DOCUMENTS

| | | | |
|---|---|---|---|
| 4,934,352 A * | 6/1990 | Sullivan, Jr. ............. 600/213 |
| 5,769,782 A * | 6/1998 | Phan ....................... 600/202 |
| 5,879,291 A * | 3/1999 | Kolata et al. ............ 600/227 |
| 5,897,490 A * | 4/1999 | Fox et al. ................ 600/227 |
| 6,074,343 A | 6/2000 | Nathanson et al. |
| 6,200,263 B1 * | 3/2001 | Person ..................... 600/227 |
| 6,464,634 B1 | 10/2002 | Fraser |
| 6,729,205 B1 * | 5/2004 | Phillips ................ 74/577 M |
| 2001/0009971 A1 | 7/2001 | Sherts et al. |
| 2002/0013514 A1 | 1/2002 | Brau |
| 2002/0095070 A1 | 7/2002 | Furnish et al. |

FOREIGN PATENT DOCUMENTS

EP  0 908 140 A1  4/1999
EP  0 931 509 A1  7/1999

* cited by examiner

*Primary Examiner*—Pedro Philogene
(74) *Attorney, Agent, or Firm*—Hamilton, Brook, Smith & Reynolds, P.C.

(57) ABSTRACT

A surgical retractor system comprises a support frame and an instrument mounting assembly. The instrument mounting assembly includes a fastening member for securing the mounting assembly to the support frame, a loading member for attaching to the mounting assembly, and a lockable rotational member providing for rotational or angular motion of the instruments about the support frame.

12 Claims, 17 Drawing Sheets

SURGICAL RETRACTOR

BACKGROUND OF THE INVENTION

Even with the advent of minimally invasive surgical techniques, many surgical procedures still require an exposed surgical field for the surgeon to successfully perform. Often, the greater the visibility and access a surgeon has to a surgical site, the greater the probability that a successful outcome will result. Once entry is made into a patient, soft tissue is dissected away further exposing the field. However, the exposed field must be maintained using instruments that do not obstruct either visual or physical access.

Surgical retractors are used to maintain exposure and access to a surgical field. There are a variety of retractors, and different surgical protocols require different styles of retractors. For example, in lumbar surgery the retractor needs to be strong enough to overcome the force exerted by the large muscle mass that has been dissected away from the field of exposure, while maintaining a visual field and access by the surgeon. Additionally, retractors are required to partition other soft-tissue components of the surgical field.

SUMMARY OF THE INVENTION

The invention is generally related to surgical retractor system. As such, there is provided a surgical retractor blade and system useful for surgical procedures. The surgical retractor system comprises a support frame and an instrument mounting assembly. The instrument mounting assembly includes a fastening member for securing the mounting assembly to the support frame, a loading member for attaching to the mounting assembly, and a lockable rotational member providing for rotational or angular motion of the instruments about the support frame.

The surgical retractor system further comprises an adjustable blade holder attached to the loading member of the mounting assembly, and a retraction blade attached to the adjustable blade holder. The blade holder includes a moveable handle, a shaft for engaging the loading member of the mounting assembly, and an adjustable retention clip for securing the retraction blade in a fixed position.

The moveable handle slides in a perpendicular plane relative to a vertical axis of the retraction blade controls an amount of tissue retraction. The moveable handle also rotates about an axis of the shaft to control adjustment of the adjustable retention clip. The shaft can be a ratchet bar.

The retraction blade includes markings associated with a unit of measure, such as metric units or imperial units. The retraction blade can be radiolucent. The fastening member can be a thumbscrew, a wing screw, and a thumb wing screw. The loading member can be a ratchet-type assembly, such as a pawl assembly. The lockable rotational member can be a ball and socket-type assembly.

The retractor blades of the invention allow for rotational or angular motion about a support frame. Further, the height of the retractor blades inside the surgical cavity is adjustable.

DETAILED DESCRIPTION OF THE INVENTION

Figure 1:
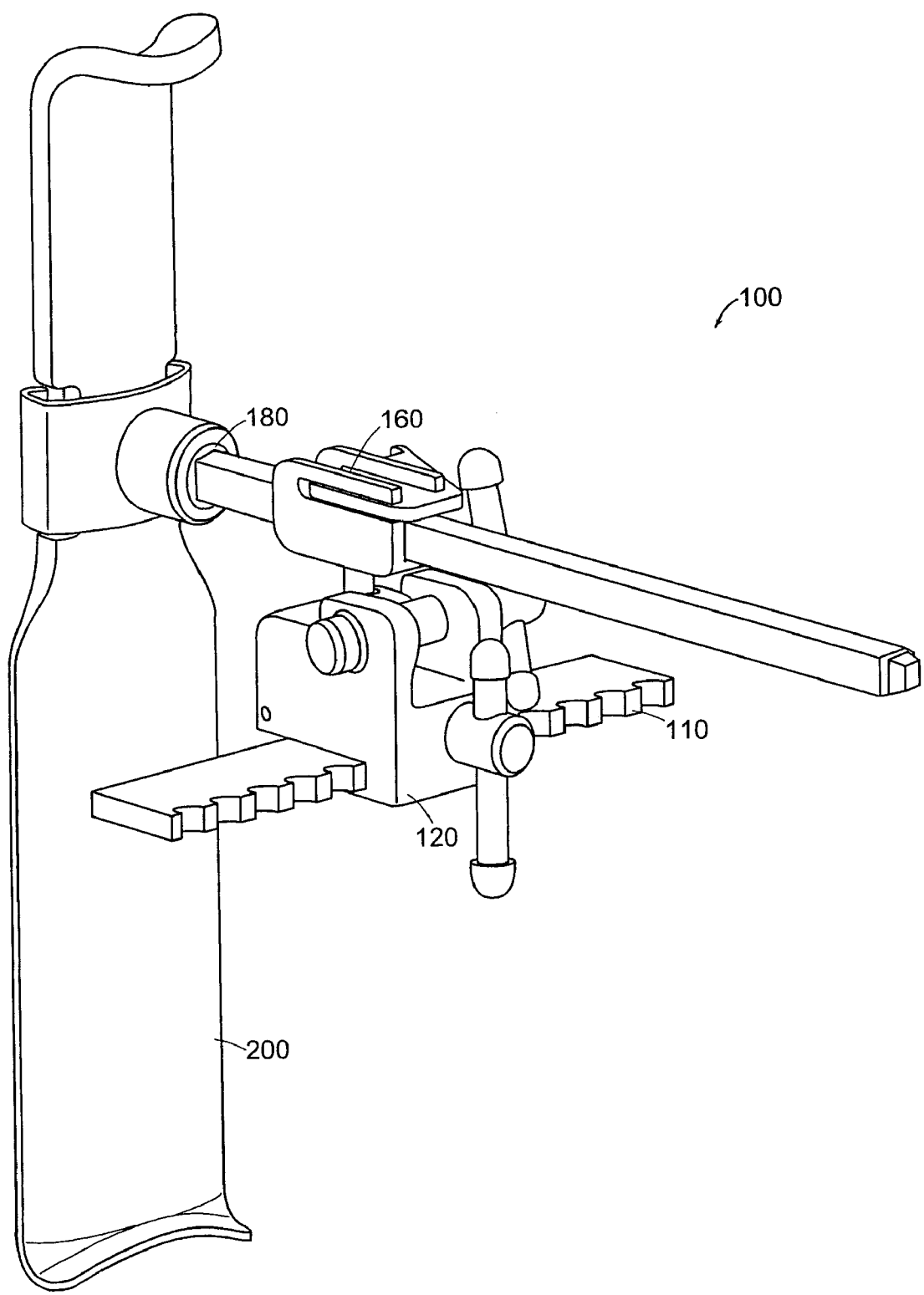
FIG. 1 is a perspective view of a partial surgical retractor system of the present invention.

The foregoing and other objects, features and advantages of the invention will be apparent from the following more particular description of preferred embodiments of the invention, as illustrated in the accompanying drawings in which like reference characters refer to the same parts throughout the different views. The same number appearing in different drawings represent the same item. The drawings are not necessarily to scale, emphasis instead being placed upon illustrating the principles of the invention.

Referring now to FIG. 1, there is shown a partial surgical retractor system 100 of the present invention. The retractor system 100 is attached to an operating table (not shown) in a manner well known to those having ordinary skill in the art. The retractor system 100 includes a frame 110, which is preferably suspended above the patient (not shown), a mounting assembly 120 attached to the frame 110, the mounting assembly 120 includes a ratchet holder assembly 160 rotatably attached to the mounting assembly 120, a blade holder assembly 180 slidably attached to the ratchet holder assembly 160, and a retractor blade 200 slidably attached to the blade holder assembly 180. It should be understood by one skilled in the art that other surgical instruments can also be mounted to the mounting assembly during a surgical procedure. The system 100 may also include a supporting arm (not shown) which may be connected to a support post (not shown) or similar elements to affix and support the retractor system in a desired position.

Figure 2A:
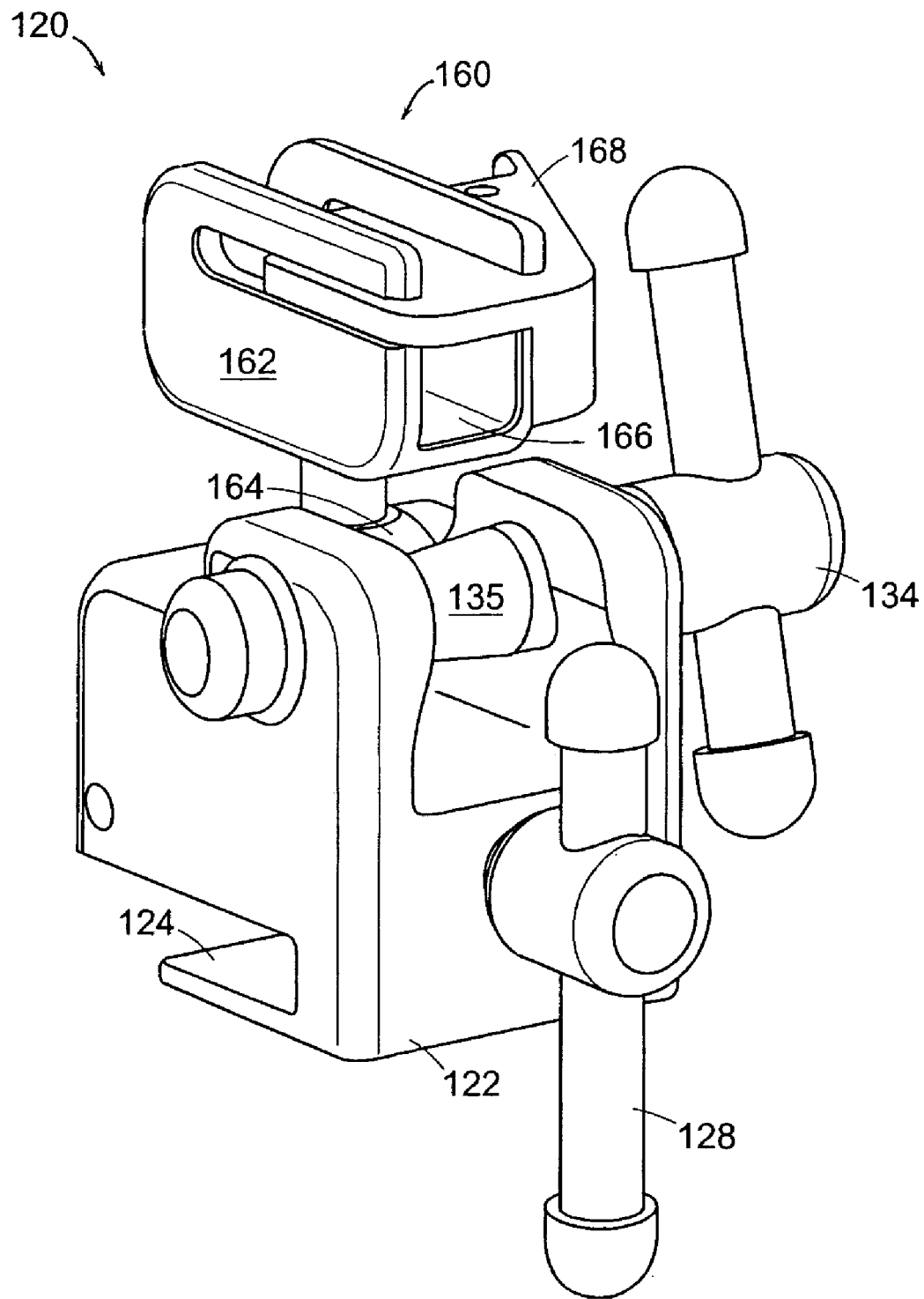
FIG. 2A is a perspective view of a mounting assembly of the surgical retractor system of FIG. 1.
Figure 2B:
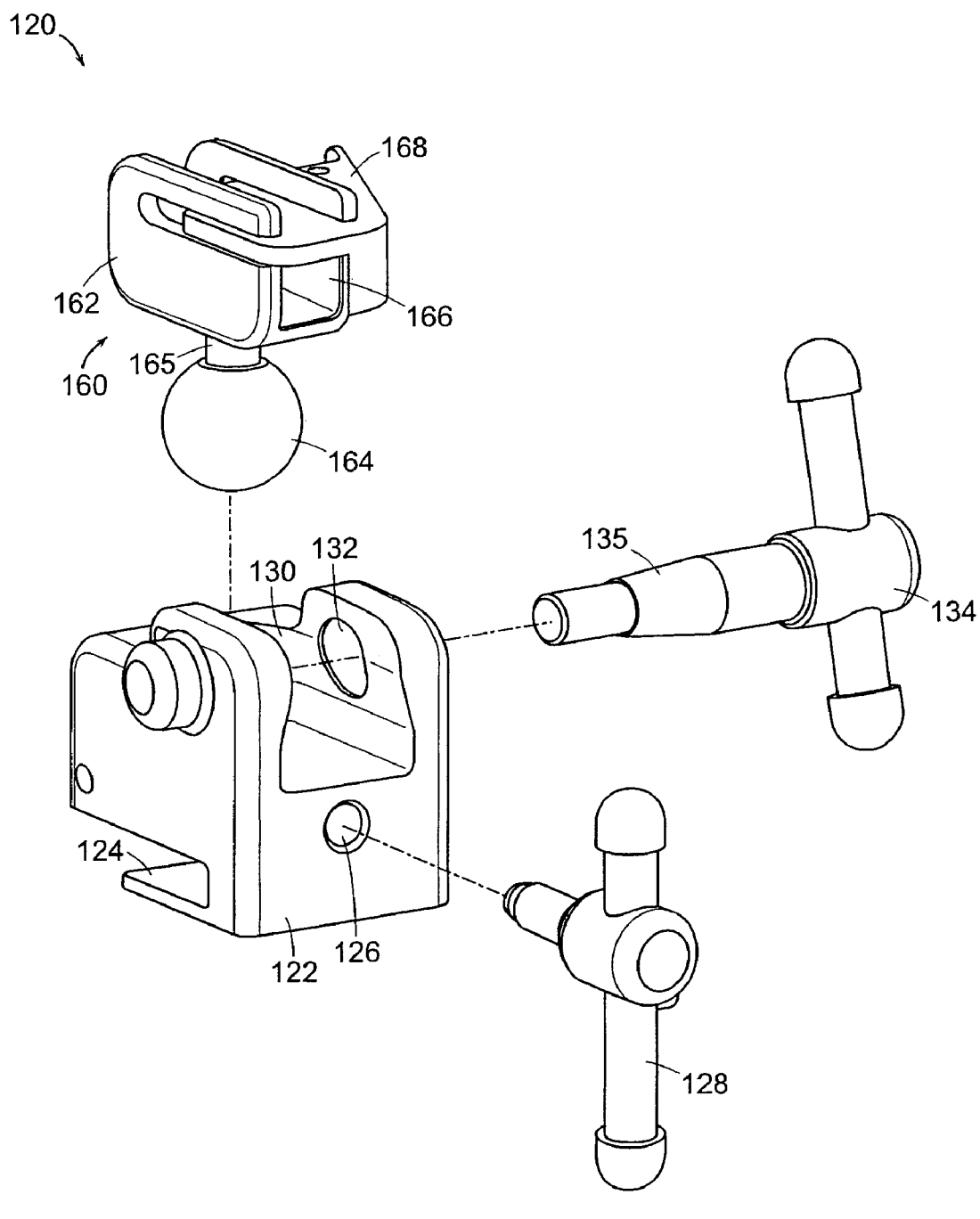
FIG. 2B is an exploded, disassembled view of the mounting assembly shown in FIG. 2A.
Figure 2C:
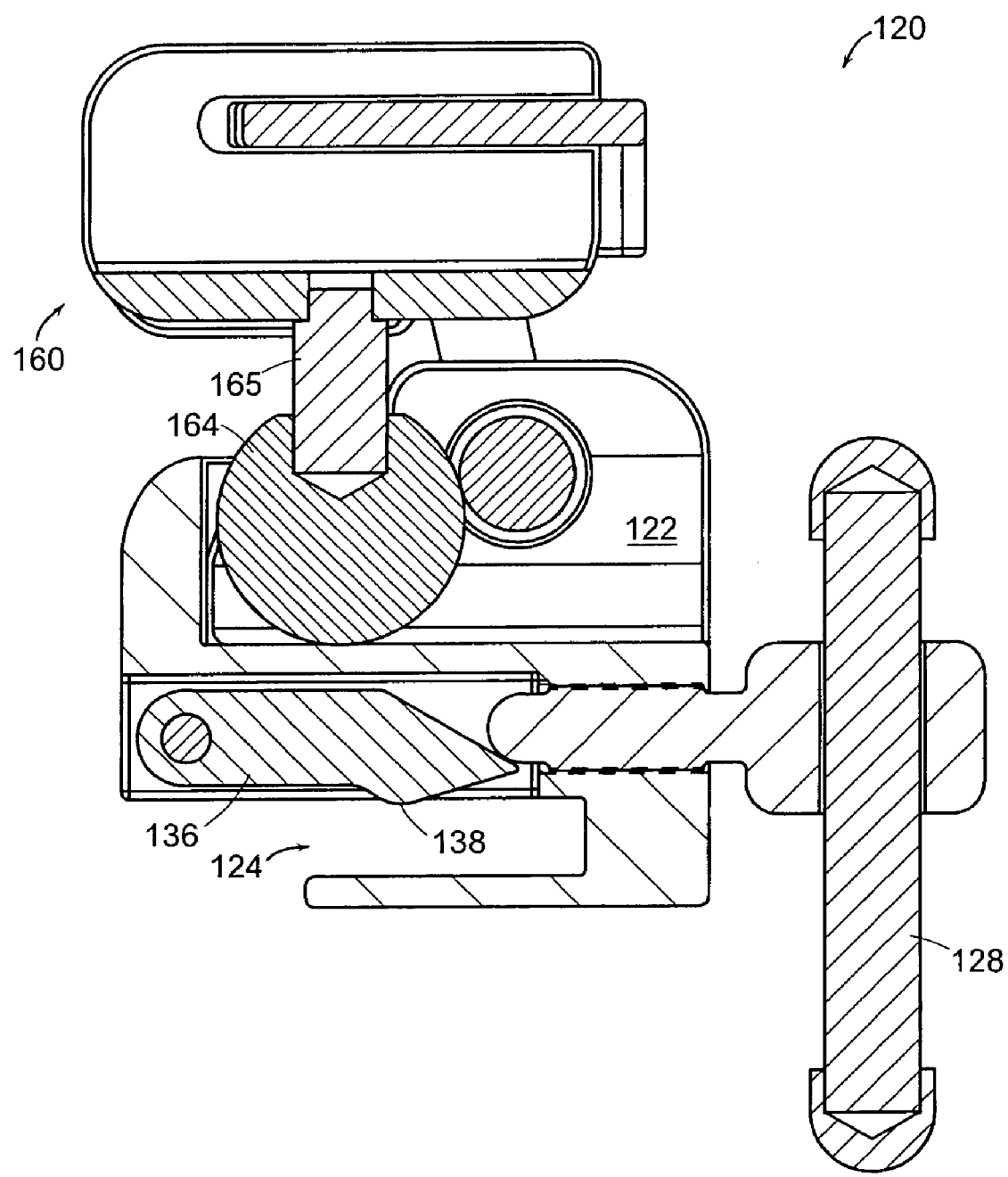
FIG. 2C is a cross-sectional view of the mounting assembly shown in FIG. 2A.
Figure 3:
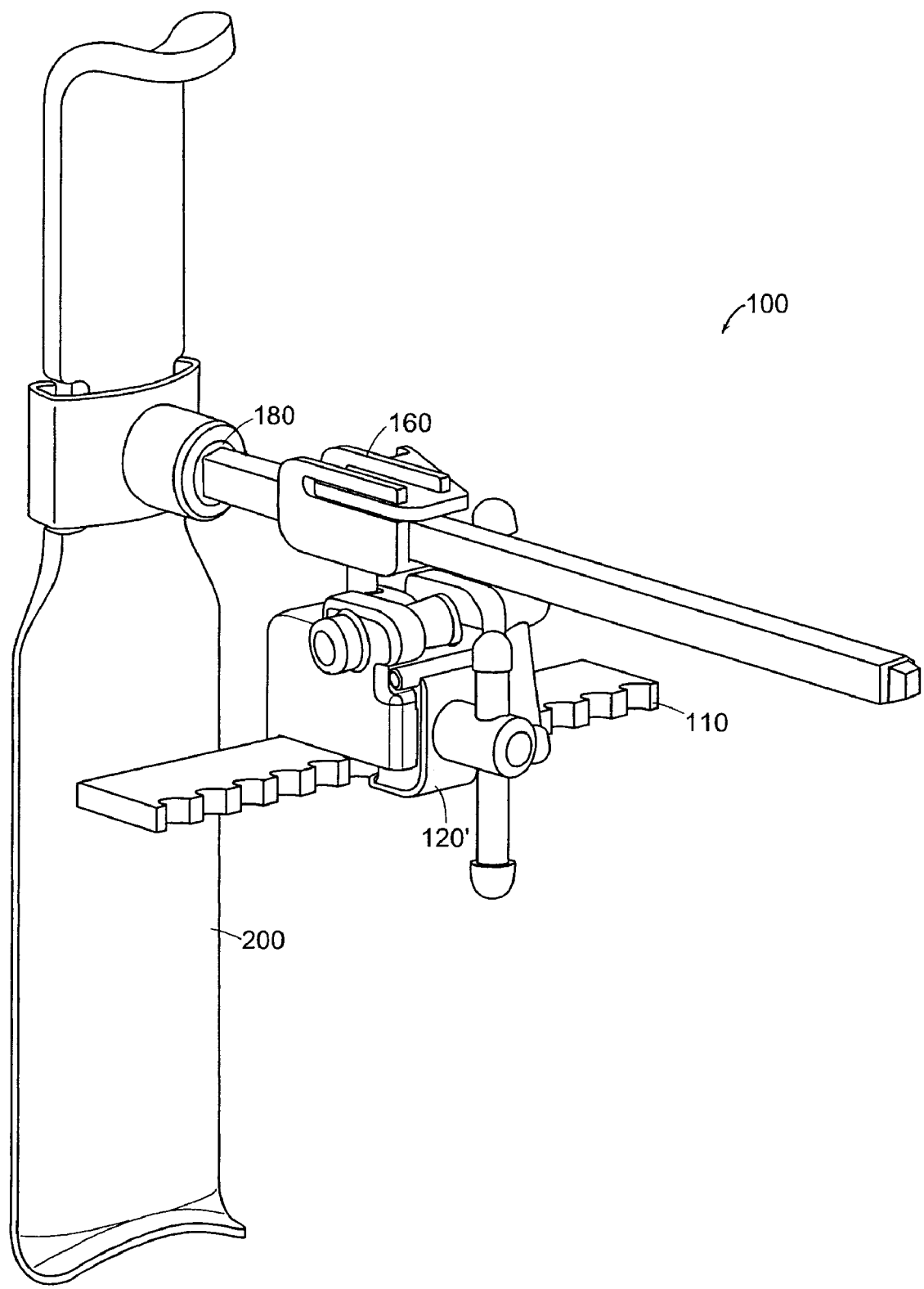
FIG. 3 is a perspective view of a partial surgical retractor system according to another embodiment of the invention.
Figure 4A:
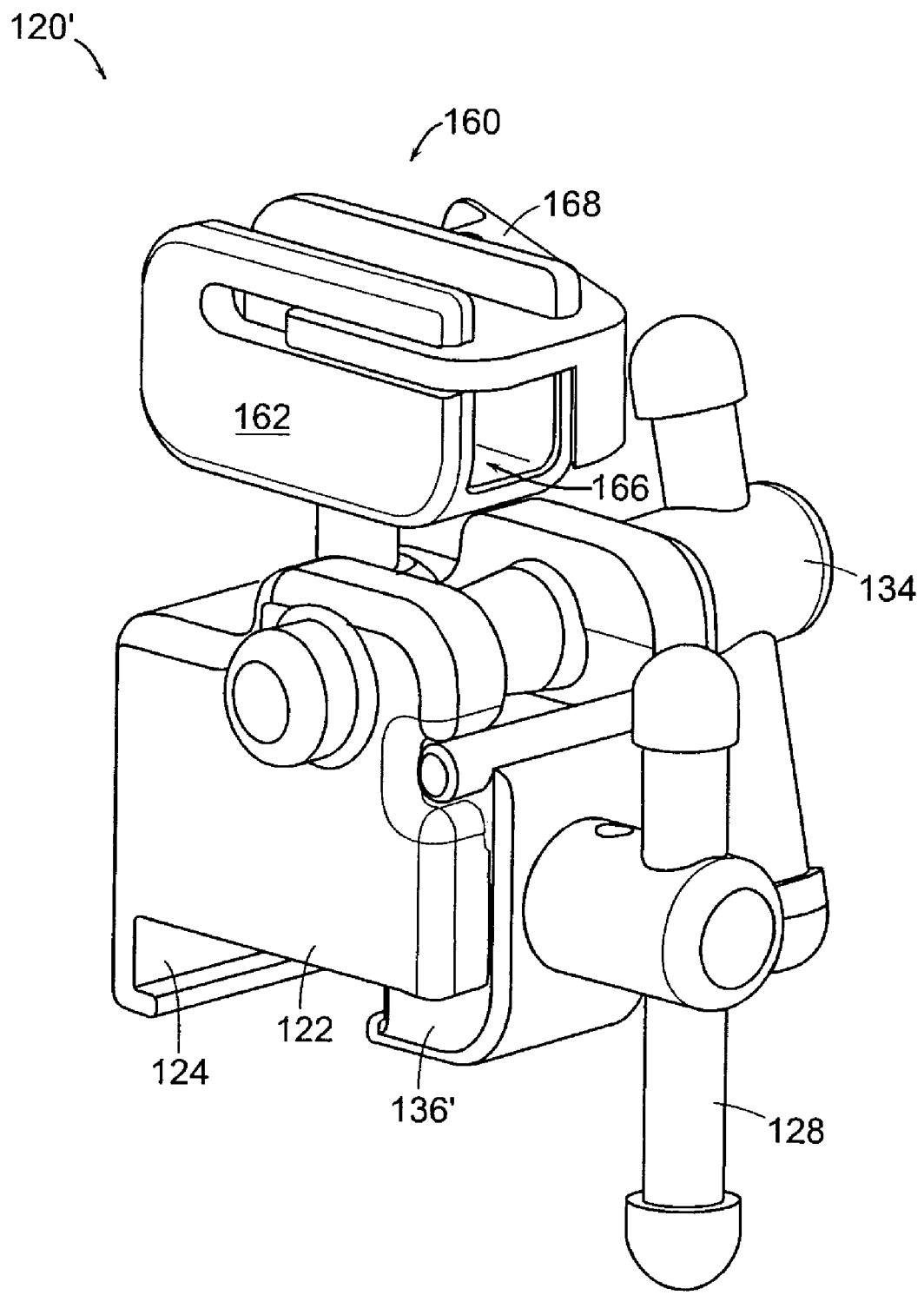
FIG. 4A is a perspective view of a mounting assembly of the surgical retractor system of FIG. 3.
Figure 4B:
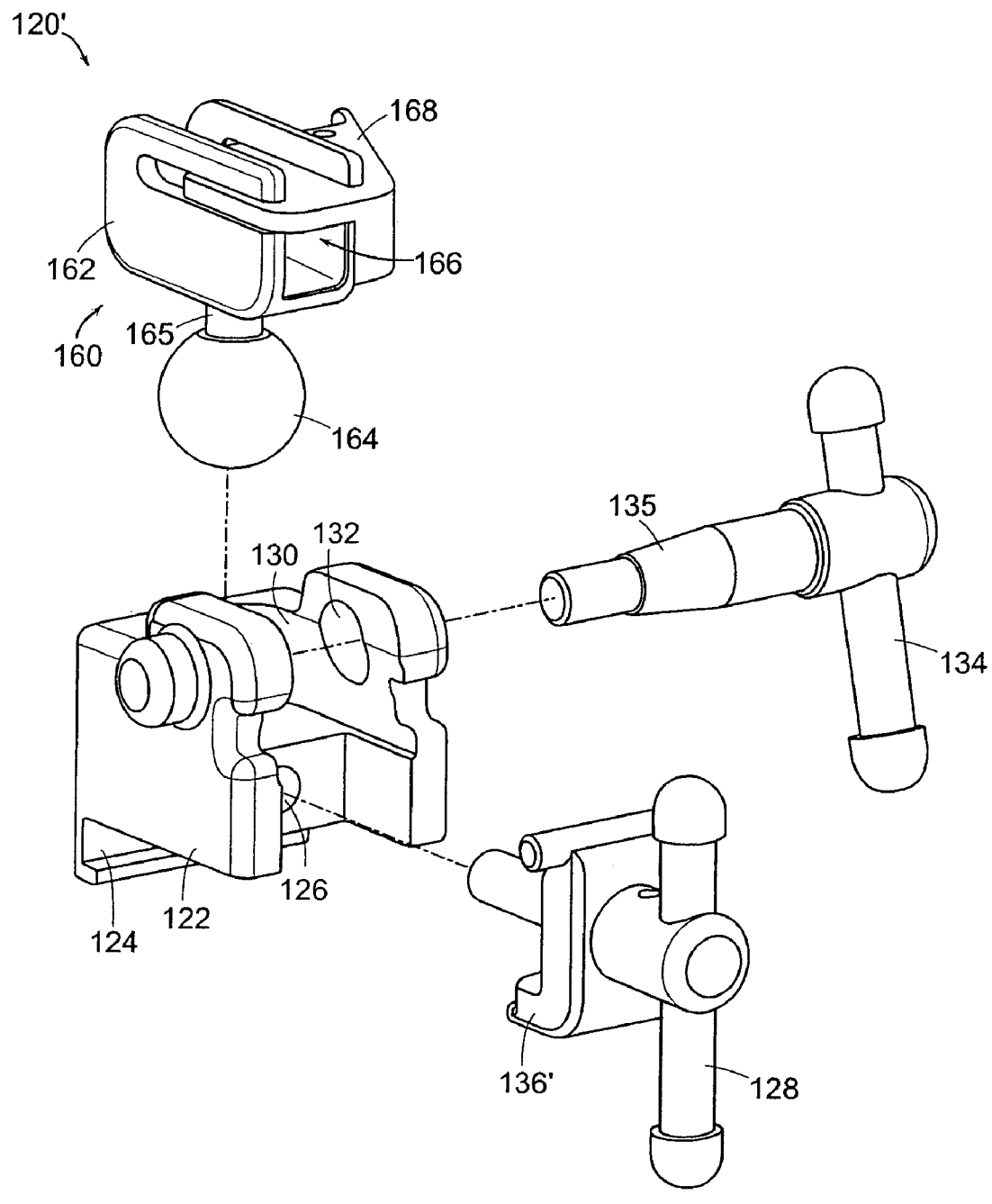
FIG. 4B is an exploded, disassembled view of the mounting assembly shown in FIG. 4A.
Figure 4C:
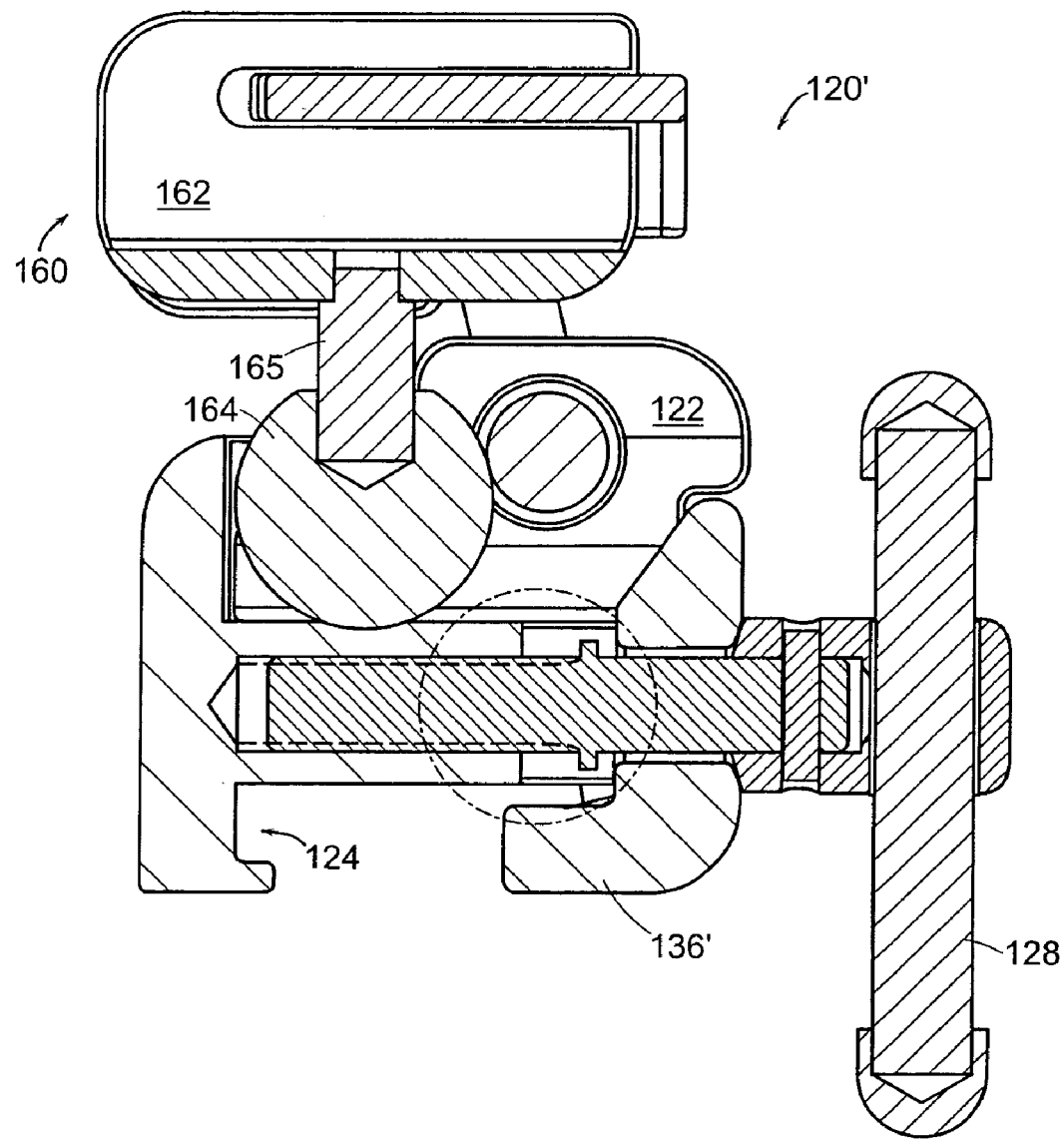
FIG. 4C is a cross-sectional view of the mounting assembly shown in FIG. 4A.
Figure 5:
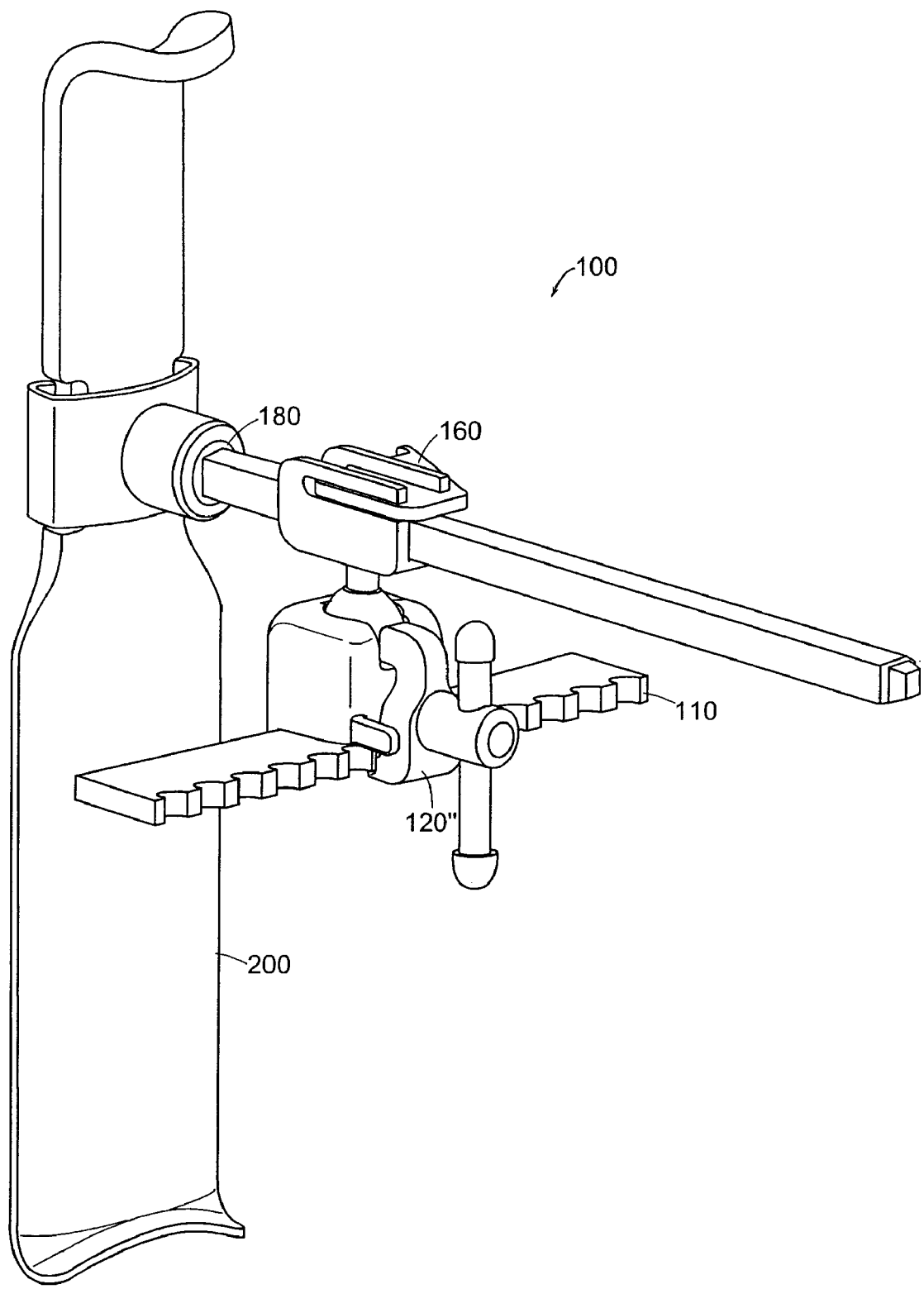
FIG. 5 is a perspective view of a partial surgical retractor system according to a further embodiment of the invention.

As shown in FIGS. 2A, 2B, and 2C, the mounting assembly 120 includes a mounting base 122, the mounting base 122 defines a frame channel 124, recessed bores 126, 132, and a socket 130. The frame slot 124 accepts the frame 110 of FIG. 1. A driver handle assembly 128 engages a locking assembly 136 through recessed bore 126. When the driver handle assembly 128 is tightened in manner well known in the art, a nub 138 of the locking assembly 136 engages and secures the mounting assembly 120 to the frame 110 of FIG. 1. The socket 130 accepts a rotational ball 164 of the ratchet holder assembly 160. A tapered portion 135 of a locking rod assembly 134 engages the rotational ball 164 through the recessed bore 132. When the locking rod assembly 134 is tightened in a manner well known in the art, the tapered portion 135 secures the ratchet holder assembly 160 in a desired position relative to the mounting base 122. However, when the locking rod assembly 134 is loosened, the ratchet holder assembly 160 can be freely rotated and angled relative to the mounting base 122. It should be understood by one skilled in the art that the driver handle assembly 128, and the locking rod assembly 134 can be any type of hand-operable tightening/loosening device, such as a thumb screw, wing screw, and fly screw.

The ratchet holder assembly 160 includes a ratchet base 162, a rotational ball 164 extended from the mounting base 162 by extension 165, and a latching mechanism 168. The ratchet base 162 defines a shaft channel 166 for accepting the blade holder assembly 180 (FIG. 1) therethrough. The latching mechanism 168 includes a gear assembly (not shown) which extends into shaft channel 166 for engaging a geared shaft of the blade holder assembly 180 of FIG. 1. When engaged, the latching mechanism 168 allows the geared shaft of blade holder assembly 180 (FIG. 1) to be incrementally moved in a direction away from the surgical site. When disengaged, the shaft of blade holder assembly 130 (FIG. 1) is freely moveable throughout the shaft channel 166. The latching mechanism 168 can be of any type well known in the art, such as a pawl assembly.

FIGS. 3, 4A, 4B and 4C illustrate an alternative embodiment of the mounting assembly of the invention. As shown in FIGS. 3A, 3B, and 3C, the mounting assembly 120' includes a mounting base 122, the mounting base 122 defines a frame slot 124, recessed bores 126, 132, and a socket 130. The frame slot 124 accepts the frame 110 of FIG. 3. A driver handle assembly includes a locking assembly 136' and engages the recessed bore 126. When the driver handle assembly 128 is tightened in manner well known in the art, the locking assembly 136' engages and secures the frame 110 of FIG. 3. The remaining features of the mounting assembly 120' operate in a similar fashion to mounting assembly 120 of FIGS. 1, 2A, 2B, and 2C described above.

Figure 6A:
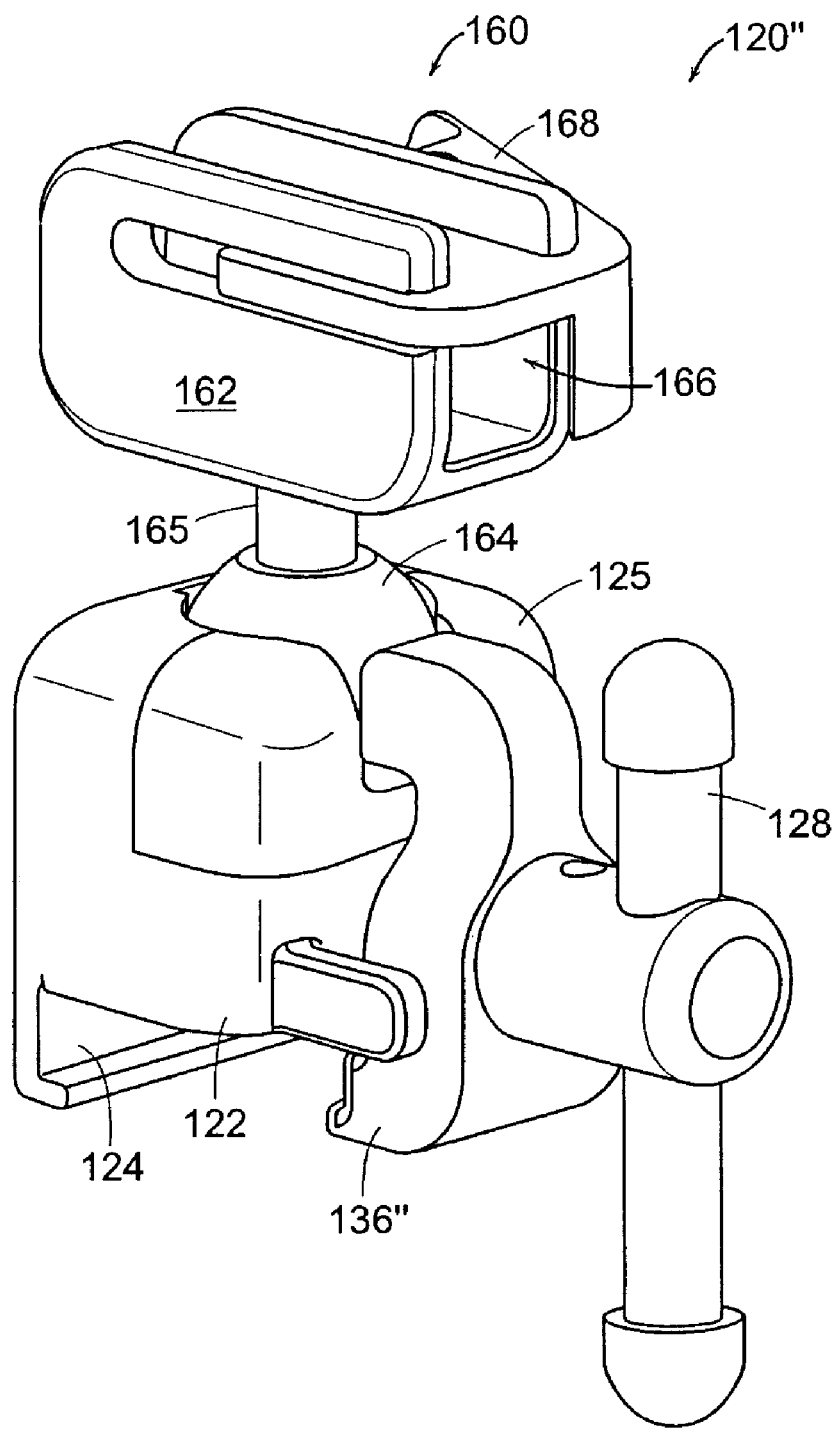
FIG. 6A is a perspective view of a mounting assembly of the surgical retractor system of FIG. 5.
Figure 6B:
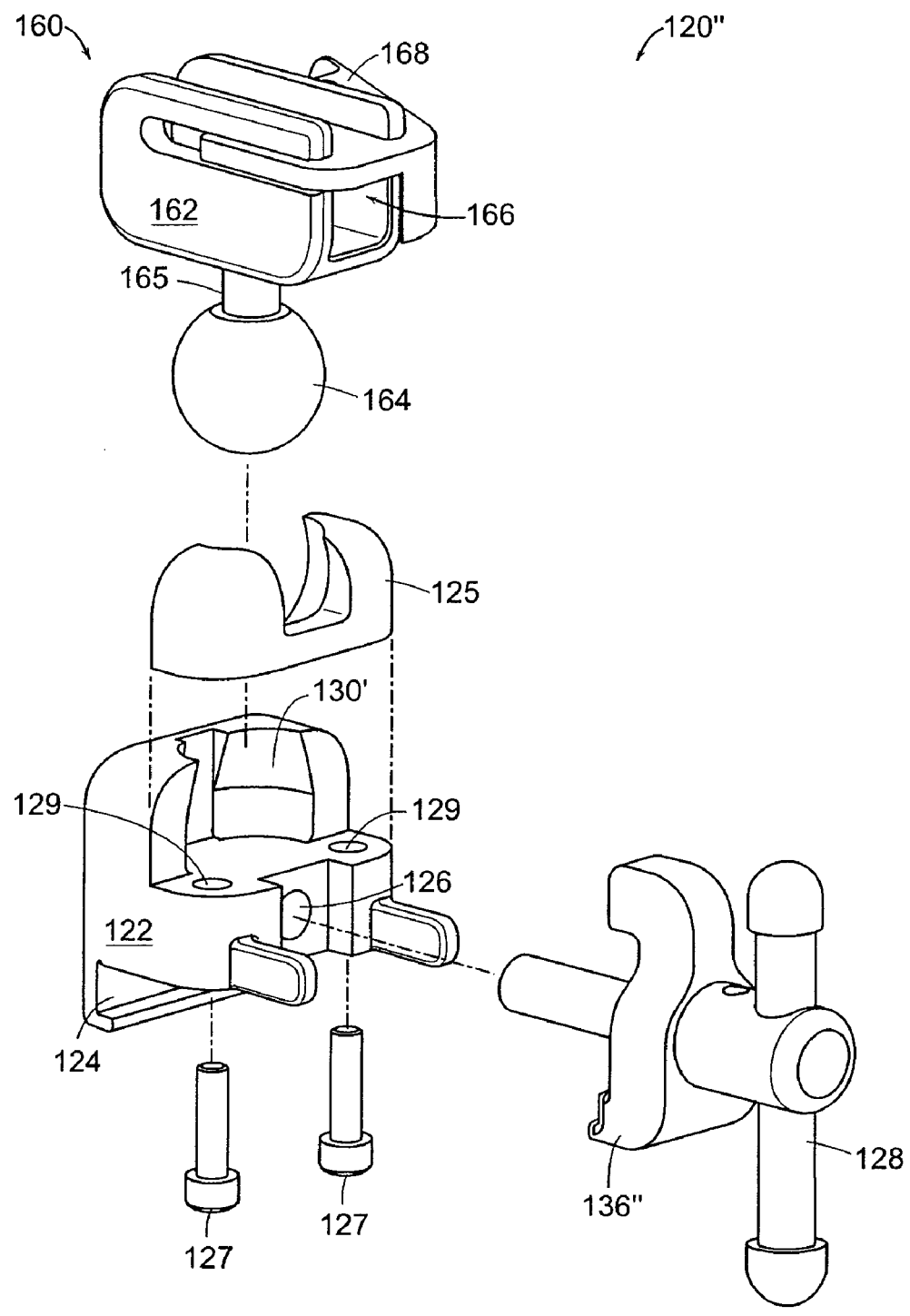
FIG. 6B is an exploded, disassembled view of the mounting assembly shown in FIG. 6A.
Figure 6C:
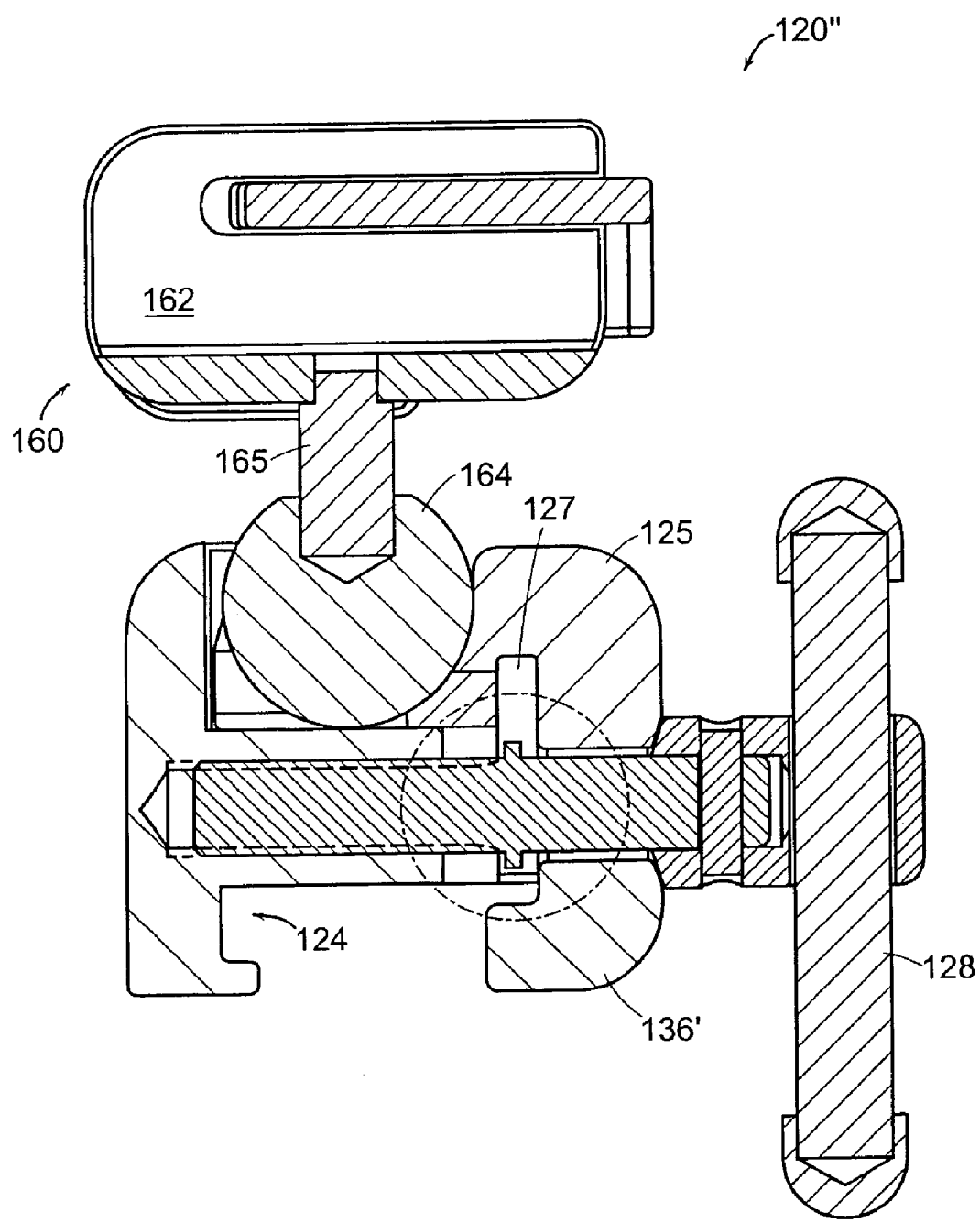
FIG. 6C is a cross-sectional view of the mounting assembly shown in FIG. 6A.

FIGS. 5, 6A, 6B and 6C illustrate a further embodiment of the mounting assembly of the invention. As shown in FIGS. 6A, 6B, and 6C, the mounting assembly 120" includes a mounting base 122, the mounting base 122 defines a frame channel 124, recessed bores 126, 129, and a partial socket 130'. The frame channel 124 accepts the frame 110 of FIG. 5. The partial socket 130' accepts a rotational ball 164 of the ratchet holder assembly 160. The ratchet holder 160 assembly is held in rotatable and angular connection with the mounting base 122 by a socket enclosure 125. Mounting bolts 127 attach the socket enclosure 125 to the mounting base 122 through recessed holes 129. The frame channel 124 accepts the frame 110 of FIG. 5. A driver handle assembly 128 includes a locking assembly 136" and engages the recessed bore 126. When the driver handle assembly 128 is tightened in manner well known in the art, the locking assembly 136" engages and secures rotational ball 164 and the frame 110 of FIG. 3. The remaining features of the mounting assembly 120" operate in a similar fashion to mounting assembly 120 of FIGS. 1, 2A, 2B, and 2C described above.

Figure 7:
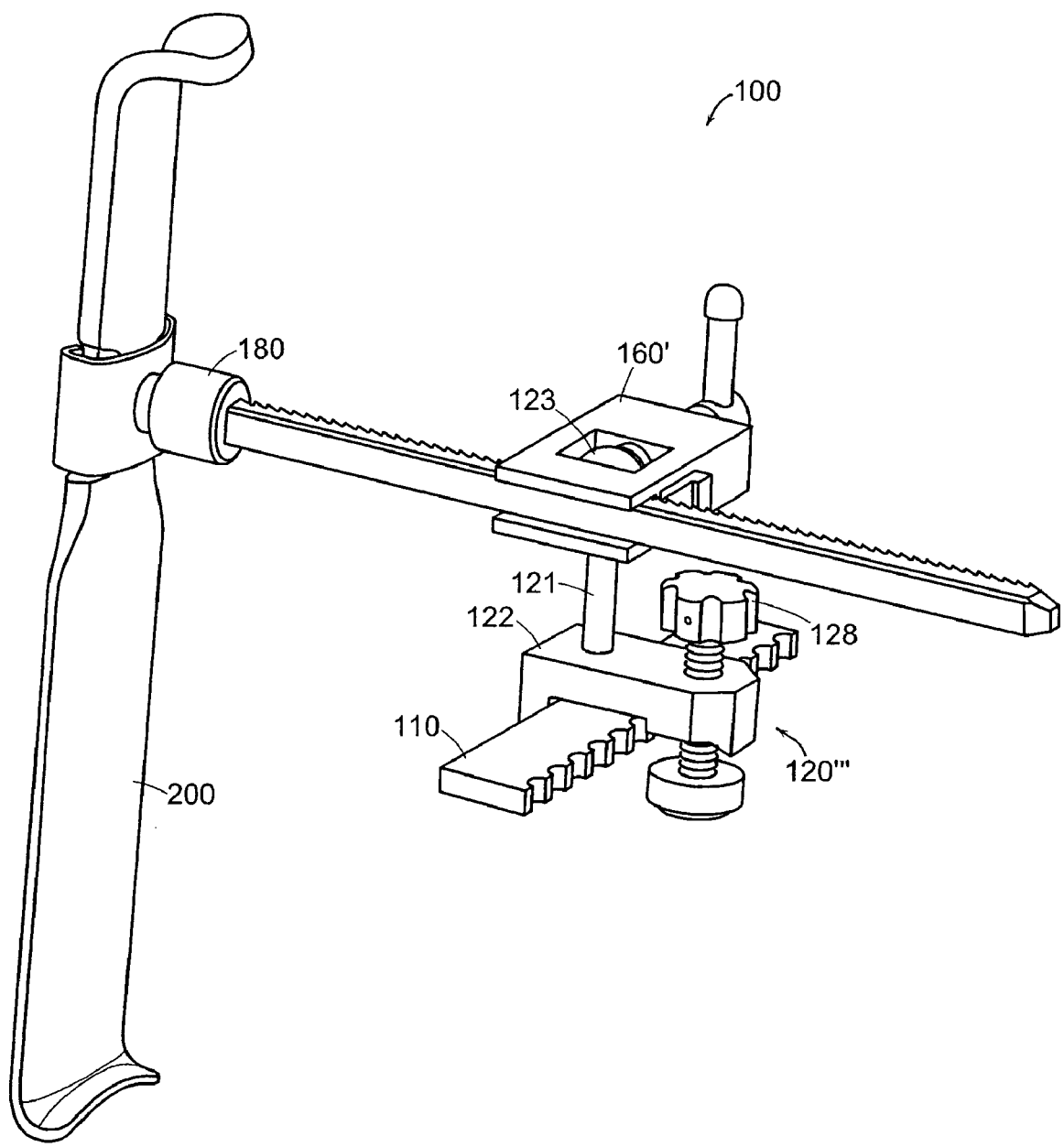
FIG. 7 is a perspective view of a partial surgical retractor system according to another embodiment of the invention.
Figure 8:
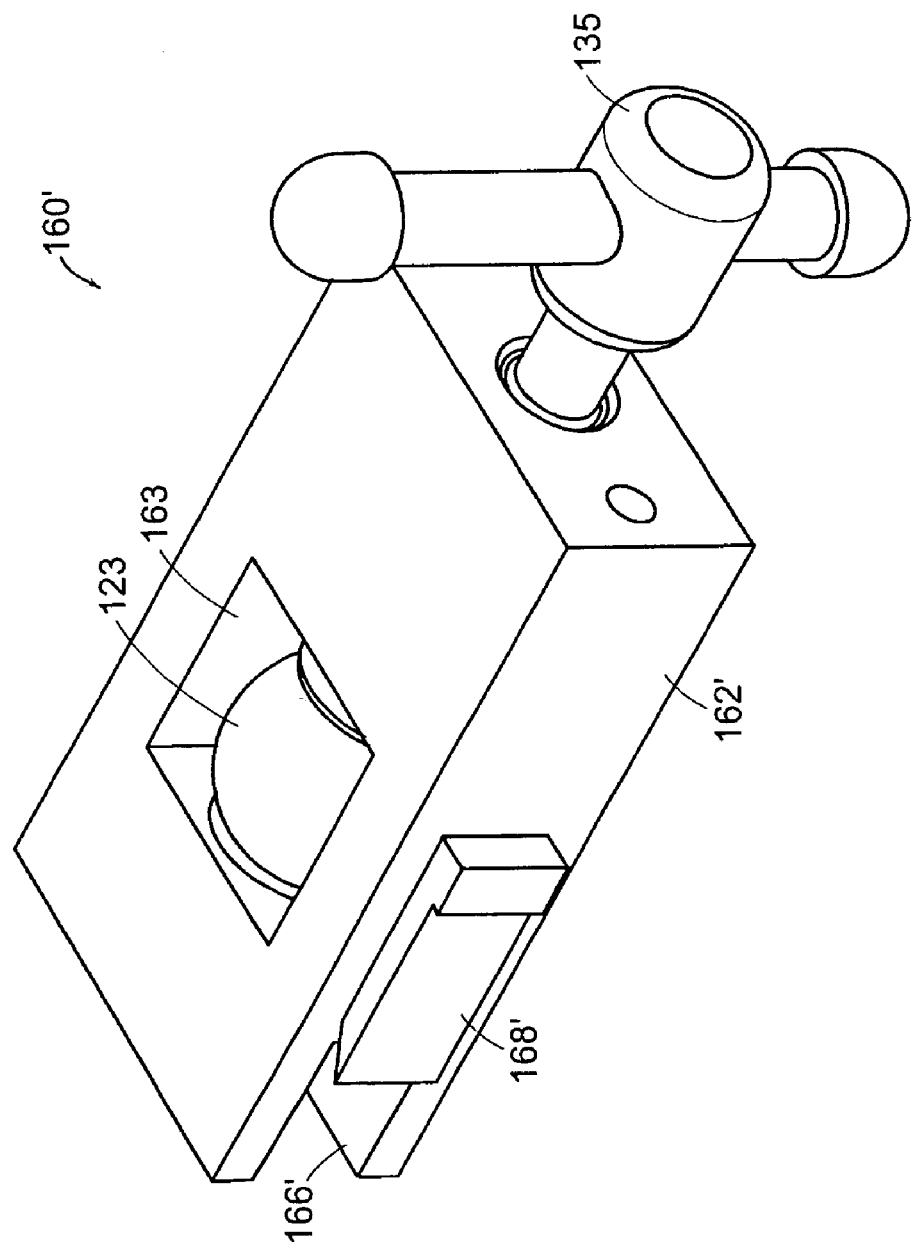
FIG. 8 is a perspective view of a ratchet holder assembly shown in FIG. 7.

FIGS. 7 and 8 illustrate another alternative embodiment of the mounting assembly of the invention. As shown in FIG. 7, the mounting assembly 120''' includes a mounting base 122, the mounting base 122 defines a frame slot, a recessed bore, a ball extender 121, a rotational ball 123 and a ratchet holder assembly 160'. The frame channel accepts the frame 110. A driver handle assembly 128 engages and secures the mounting assembly 120''' to the frame 110. As shown in FIG. 8, the ratchet holder assembly 160' includes a ratchet base 162', a locking rod assembly 135', and a latching mechanism 168'. The ratchet base 162' defines a shaft slot 166' and a rotatable ball channel 163. The shaft slot 166' accepts the blade holder assembly 180 (FIG. 7) slidably therethrough and the rotatable ball channel 163 accepts the rotational ball 123 of the mounting assembly 120'''. The latching mechanism 168' extends into shaft slot 166' for engaging a shaft of the blade holder assembly 180 of FIG. 7. When engaged, the latching mechanism 168' allows the shaft of blade holder assembly 180 (FIG. 7) to be incrementally moved in a direction away from the surgical site to retract tissue. When disengaged, the shaft of blade holder assembly 180 (FIG. 7) is freely moveable throughout the shaft slot 166'. The latching mechanism 168' can be of any type well known in the art, such as a pawl assembly.

Figure 9A:
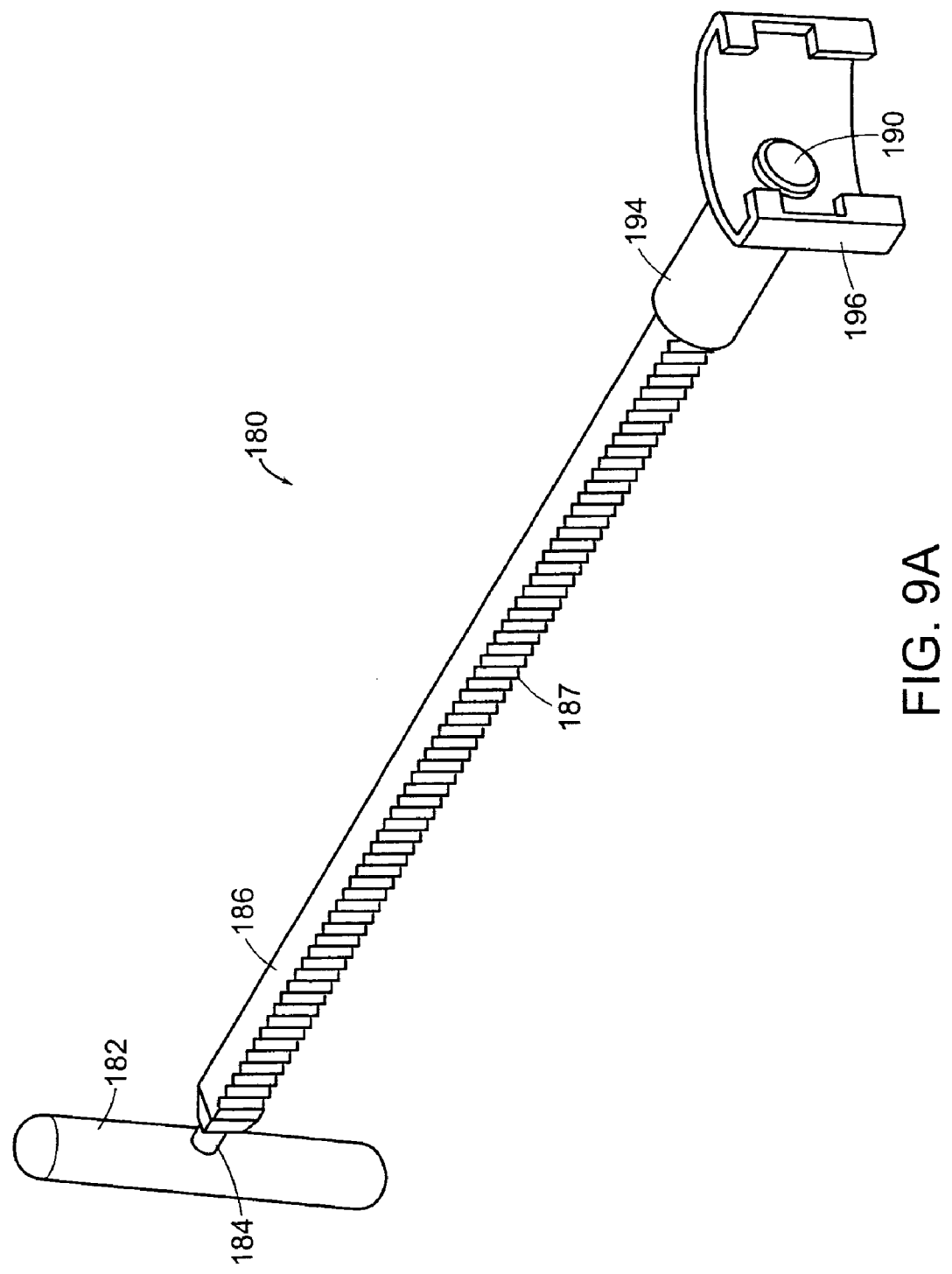
FIG. 9A is a perspective view of a blade holder assembly of the present invention.
Figure 9B:
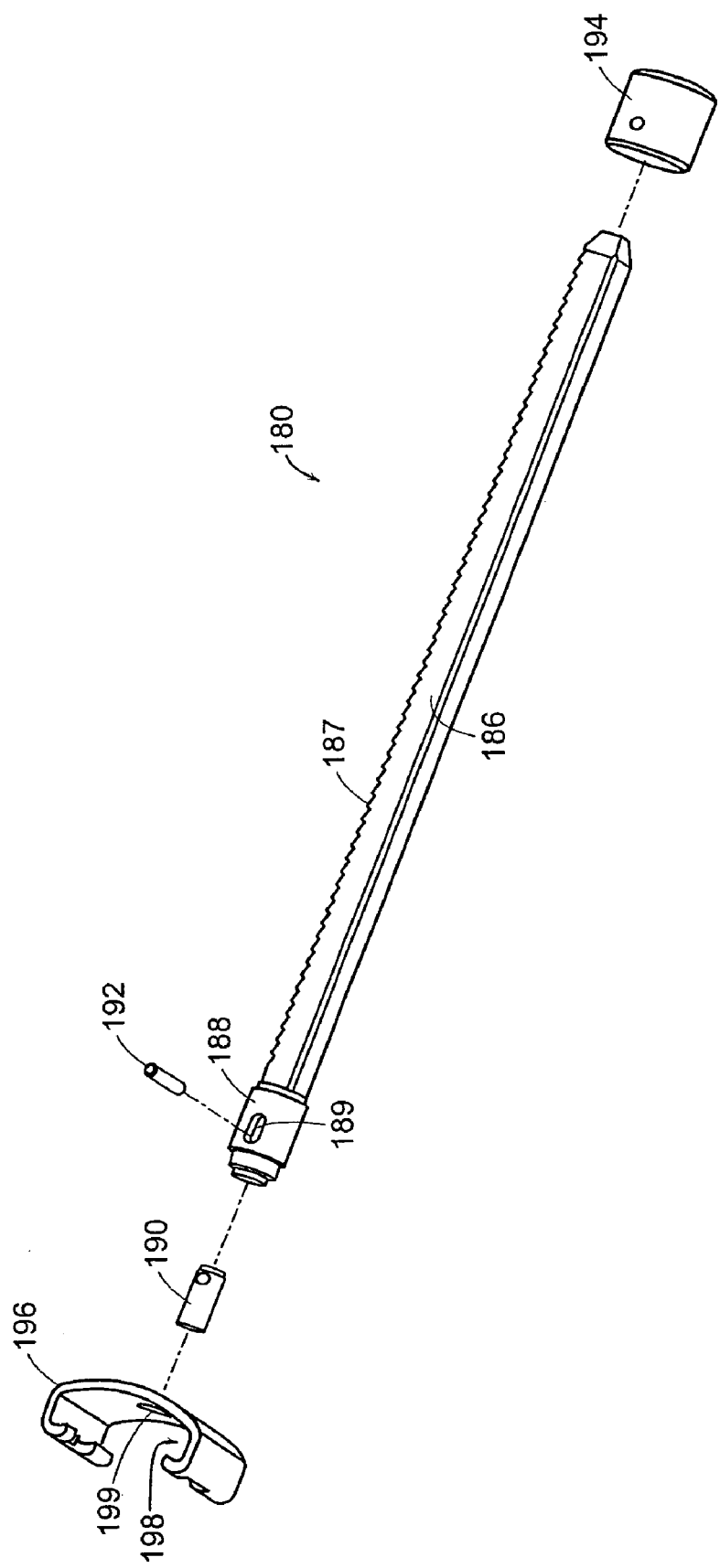
FIG. 9B is an exploded, disassembled view of the blade holder assembly shown in FIG. 9A.

FIGS. 9A, 9B, and 9C illustrate the blade holder assembly 180 of the present invention. The blade holder assembly 180 includes a handle 182, an internal shaft 184, and external shaft 186, a spherical coupling 188, a driving pin 190, a dowel pin 192, a locking knob 194 and a blade holder 196.

The external shaft 186 defines a radial bore which houses the internal shaft 184. The external shaft 186 includes gears 187 which engage the locking mechanism of the ratchet holder assembly described above. The external shaft 186 can be any type of geared bar known in the art, such as a ratchet bar. The spherical coupling 188 is connected to a proximal end of the external shaft 184 and houses the driving pin 190. The driving pin 190 is connected to a proximal end of the internal shaft 184 and the handle 182 is connected to a distal end of the internal shaft 184. A dowel pin 192 connects the driving pin 190, internal shaft 184, and handle 182 to the spherical coupling 188 through a dowel pin slot 189.

The driving pin 190, dowel pin 192, internal shaft 184, and handle 182 are moveable in the axial plane of the internal shaft 184. The degree of movement is restricted by the length of the dowel pin slot 189. The blade holder 196 is connected to a distal end of the spherical coupling 188 and secured to the assembly via the locking knob 194. The blade holder 196 defines a channel 198 for accepting the retraction blade 200 and a retention bore 199 allows the driving pin 190 to engage a surface of the retraction blade 200.

Figure 10:
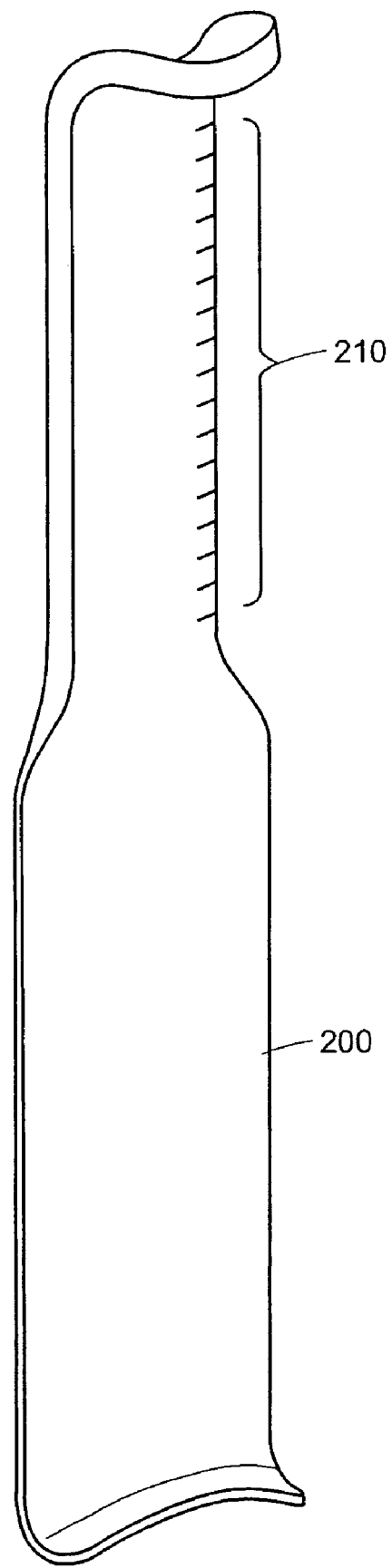
FIG. 10 is a perspective view of a retractor blade of to the present invention.

Now referring to FIG. 10, a retractor blade 200 of the present invention is shown. The retractor blade 200 can be made from a radiolucent material to allow X-rays to be taken during the surgical procedure without interference from the retraction blade 200. The retraction blade 200 can be incremented 210 associated with a unit of measure for determining the depth of the retraction blade 200 within the surgical cavity. The units of measure can be metric, imperial or any other unit of measure known in the art. The length of the retraction blade 200 can vary between 4 and 20 inches. The retraction blades 200 are shaped to effectively hold soft tissue and vascular tissue as shown in FIG. 10. Further, the retraction blades 200 are relatively stiff, such that only minimal deflection occurs during retraction.

The operation of the surgical retractor system 100 will now be described with reference to the above-mention assemblies and figures. In general, if tissue retraction is needed, a frame is positioned over a surgical site during a surgical procedure. At least one mounting assembly is attached to the frame. However, it is preferable to diametrically attach pairs of mounting assemblies to the frame. A blade holder assembly is attached each mounting assembly and the angle of each blade holder assembly with relation to its mounting assembly is adjusted to a desired position over the surgical site. A retraction blade is inserted into the surgical cavity through each blade holder assembly while maintaining mechanical connection with its blade holder assembly. Each retraction blade is secured at a desired depth within the surgical cavity. Tissue is retracted from the surgical site by moving each blade holder assembly in a direction away from the surgical site. It may be desirable to x-ray the surgical site once the surgical site is fully distracted. To that end, each radiolucent blade can be made from a radiolucent material to prevent x-ray interference. When the surgical procedure is finished each blade holder assembly is released and the surgical retraction system is removed.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A surgical retractor system, comprising:
   (a) a support frame;
   (b) at least one instrument mounting assembly including:
      (i) a first driver handle assembly, the first driver handle assembly securing the mounting assembly to the support frame;
      (ii) a loading member, the loading member coupling instruments to the mounting assembly; and
      (iii) a rotational member, the rotational member providing for rotational or angular motion of the instruments about the support frame;
   (c) at least one adjustable blade holder coupled to the loading member of the mounting assembly, wherein the blade holder comprises:
      (1) a shaft having a proximal end and a distal end;
      (2) a retention clip coupled to the distal end of the shaft, the retention clip formed to slidably accept a retraction blade; and
      (3) a moveable handle coupled to the proximal end of the shaft, wherein actuation of the moveable handle secures the retraction blade to the retention clip or releases the retraction blade from the retention clip and wherein the moveable handle controls an amount of tissue retraction by the retraction blade; and
   (d) at least one retraction blade coupled to the blade holder.

2. The surgical retractor system of claim 1, wherein the driver handle assembly includes at least one member of a group consisting of a thumbscrew, a wing screw, and a thumb wing screw.

3. The surgical retractor system of claim 1, wherein the loading member includes a ratchet-type assembly.

4. The surgical retractor system of claim 3, wherein the ratchet-type assembly is a pawl assembly.

5. The surgical retractor system of claim 1, wherein the rotational member includes a ball and socket-type assembly.

6. The surgical retractor system of claim 1, wherein the moveable handle is slidable in a perpendicular plane relative to a vertical axis of the retraction blade to control an amount of tissue retraction.

7. The surgical retractor system of claim 1, wherein the shaft is a ratchet bar.

8. The surgical retractor system of claim 1, wherein the retraction blade includes markings associated with a unit of measure.

9. The surgical retractor system of claim 8, wherein the unit of measure includes at least one member selected form a group consisting of metric units and imperial units.

10. The surgical retractor system of claim 1, wherein the retraction blade is radiolucent.

11. The surgical retractor system of claim 1, wherein the driver handle assembly further secures the rotational member in a fixed position about the support frame.

12. The surgical retractor system of claim 1, further comprising a locking rod assembly, the locking rod assembly secures the rotational member in a fixed position about the support frame.

* * * * *